US010428374B2

(12) United States Patent
Adey et al.

(10) Patent No.: US 10,428,374 B2
(45) Date of Patent: Oct. 1, 2019

(54) LIQUID DISPENSING DEVICE

(71) Applicant: AvanSci Bio, L.L.C., Salt Lake City, UT (US)

(72) Inventors: Nils B. Adey, Salt Lake City, UT (US); Robert J. Parry, Park City, UT (US)

(73) Assignee: Kimantech, LLC, Salt Lake City, UT (US)

( * ) Notice: Subject to any disclaimer, the term of this patent is extended or adjusted under 35 U.S.C. 154(b) by 166 days.

(21) Appl. No.: 15/027,232

(22) PCT Filed: Oct. 4, 2014

(86) PCT No.: PCT/US2014/059205
§ 371 (c)(1),
(2) Date: Apr. 4, 2016

(87) PCT Pub. No.: WO2015/051347
PCT Pub. Date: Apr. 9, 2015

(65) Prior Publication Data
US 2016/0251708 A1    Sep. 1, 2016

Related U.S. Application Data

(60) Provisional application No. 61/968,987, filed on Mar. 21, 2014, provisional application No. 61/887,174, filed on Oct. 4, 2013.

(51) Int. Cl.
*C12Q 1/6848* (2018.01)
*B01L 3/02* (2006.01)
(Continued)

(52) U.S. Cl.
CPC ............. *C12Q 1/6848* (2013.01); *B01L 3/02* (2013.01); *B01L 3/0217* (2013.01); *B01L 3/502* (2013.01);
(Continued)

(58) Field of Classification Search
None
See application file for complete search history.

(56) References Cited

U.S. PATENT DOCUMENTS 5,307,953 A    5/1994  Regan
6,485,623 B1*  11/2002 Anderson ........ G01N 27/44743
                                                     132/160
(Continued)

FOREIGN PATENT DOCUMENTS

EP        2452754 A2      5/2012
WO   WO 2011018658 A1    2/2011

OTHER PUBLICATIONS

PCT Application No. PCT/US2014/59205; Filing Date Oct. 4, 2014, Nils B. Adey, International Search Report, dated Mar. 26, 2015, 20 pages.

(Continued)

*Primary Examiner* — Jill A Warden
*Assistant Examiner* — Brittany I Fisher
(74) *Attorney, Agent, or Firm* — Thorpe North & Western, LLP; David W. Osborne

(57) ABSTRACT

A liquid dispensing device for a container, and associated systems and methods, are disclosed. The liquid dispensing device can include a penetrating tip configured to penetrate a container, which is configured to have a liquid disposed therein. Relative movement of the penetrating tip and the container toward one another can be operable to create an opening in a portion of the container, and the liquid can dispense from the container through the opening.

29 Claims, 15 Drawing Sheets

(51) Int. Cl.
*C12Q 1/686* (2018.01)
*B01L 3/00* (2006.01)

(52) U.S. Cl.
CPC .......... *B01L 3/5082* (2013.01); *C12Q 1/686* (2013.01); *B01L 3/5025* (2013.01); *B01L 2200/026* (2013.01); *B01L 2200/0642* (2013.01); *B01L 2200/0684* (2013.01); *B01L 2200/141* (2013.01); *B01L 2300/042* (2013.01); *B01L 2300/044* (2013.01); *B01L 2300/0609* (2013.01); *B01L 2300/0672* (2013.01); *B01L 2300/0848* (2013.01); *B01L 2300/14* (2013.01); *B01L 2400/0478* (2013.01)

(56) References Cited

U.S. PATENT DOCUMENTS

| | | | |
|---|---|---|---|
| 6,656,428 B1* | 12/2003 | Clark | B01L 3/502 422/404 |
| 6,805,842 B1 | 10/2004 | Bodner et al. | |
| 2004/0035891 A1* | 2/2004 | Matthews | B01L 3/0296 222/386 |
| 2005/0148091 A1* | 7/2005 | Kitaguchi | B01L 3/502715 436/164 |
| 2006/0079834 A1* | 4/2006 | Tennican | A61J 1/2096 604/88 |
| 2006/0166233 A1* | 7/2006 | Wu | B01L 3/502707 435/6.16 |
| 2006/0228256 A1* | 10/2006 | McDevitt | B01J 19/0046 422/82.05 |
| 2007/0245810 A1* | 10/2007 | Carter | B01L 3/502723 73/53.01 |
| 2007/0263049 A1* | 11/2007 | Preckel | B01F 5/0683 347/85 |
| 2007/0292941 A1* | 12/2007 | Handique | B01L 3/5027 435/288.7 |
| 2008/0245314 A1 | 10/2008 | Brodowski et al. | |
| 2008/0283439 A1* | 11/2008 | Sullivan | A61M 15/0028 206/531 |
| 2008/0300536 A1 | 12/2008 | Wang et al. | |
| 2010/0126857 A1* | 5/2010 | Polwart | B01L 9/527 204/403.14 |
| 2010/0291666 A1* | 11/2010 | Collier | B01L 3/502715 435/287.2 |
| 2011/0104816 A1* | 5/2011 | Pollack | B01L 3/502715 436/174 |
| 2011/0186466 A1* | 8/2011 | Kurowski | B01L 3/502715 206/524.6 |
| 2011/0304040 A1 | 12/2011 | Kojima | |
| 2013/0092763 A1 | 4/2013 | Spearman, Sr. | |
| 2013/0228136 A1* | 9/2013 | Lyon | A01K 13/003 119/601 |
| 2014/0255275 A1* | 9/2014 | Barry | B01L 3/502715 422/547 |
| 2014/0322706 A1* | 10/2014 | Kayyem | B01L 3/502715 435/6.11 |

OTHER PUBLICATIONS

Sarkar et al.; "Shedding Light on PCR Contamination;" Nature; (1990); p. 27; vol. 343.
Sarkar et al.; "More Light on PCR Contamination;" Nature; (1990); pp. 340-341; vol. 347.
Deragon et al.; "Use of Gamma Irradiation to Eliminate DNA Contamination for PCR;" Nucleic Acids Research; (1990); p. 6149; vol. 18, No. 20.
Cimino et al.; "Post-PCR Sterilization: A Method to Control Carryover Contamination for the Polymerase Chain Reaction;" Nucleic Acids Research; (1991); pp. 99-107; vol. 19, No. 1.
Sarkar et al.; "Parameters Affecting Susceptibility of PCR Contamination to UV Inactivation;" Biotechniques; (May 1, 1991); pp. 590-594; vol. 10, No. 5.
Fox et al.; "Eliminating PCR Contamination: Is UV Irradiation the Answer?;" Journal of Virological Methods; (Aug. 1991); pp. 375-382; vol. 33, Issue 3; <doi: 10.1016/0166-0934(91)90037-Z>.
Longo et al.; "Use of Uracil DNA Glycosylase to Control Carry-Over Contamination in Polymeraxe Chain Reactions;" Gene; (Sep. 1, 1990); pp. 125-128; vol. 93, Issue 1; <doi: 10.1016/0379-1119(90)90145-H>.
Victor et al.; "Laboratory Experience and Guidelines for Avoiding False Positive Polymerase Chain Reaction Results;" European Journal of Clinical Chemistry and Clinical Biochemistry; (1993); pp. 531-535; vol. 31, No. 8.
Balin et al.; "Identification and Localization of *Chlamydia pneumoniae* in the Alzheimer's Brain;" Medical Microbiology and Immunology; (Aug. 1998); pp. 23-42; vol. 187, Issue 1; <doi: 10.1007/s004300050071>.
Lo et al.; "Setting Up a Polymerase Chain Reaction Laboratory:" *Methods in Molecular Biology*; (2006); pp. 11-18; vol. 336.

* cited by examiner

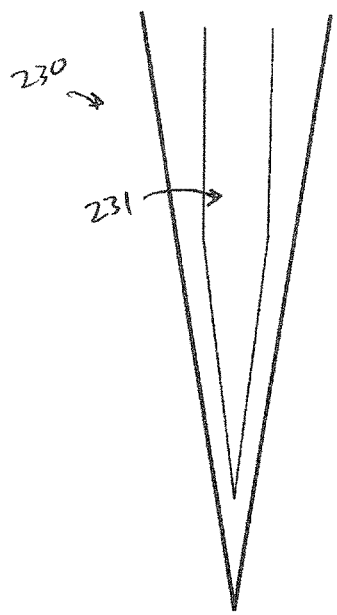
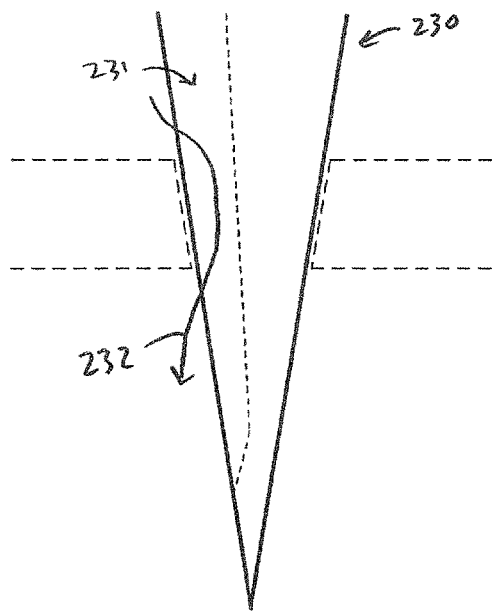
FIG. 3A            FIG. 3B
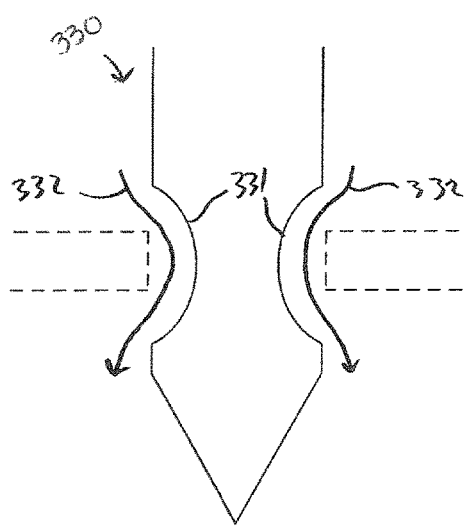
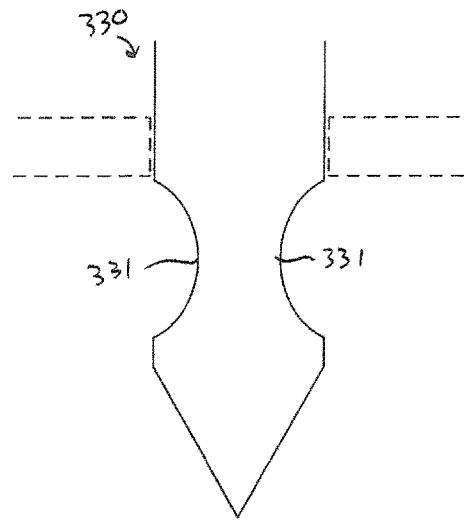
FIG. 4A            FIG. 4B

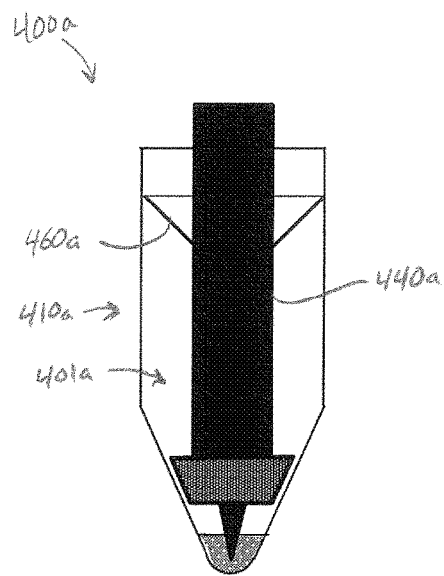
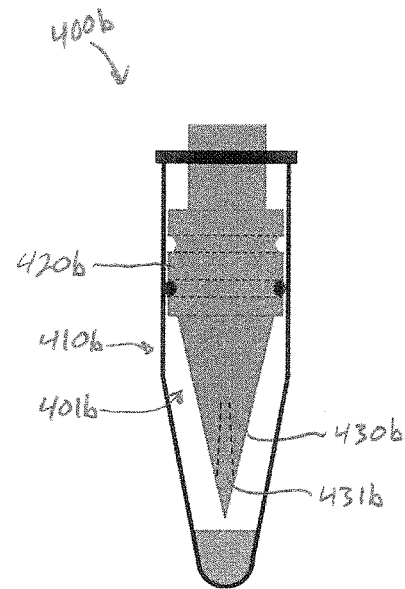
FIG. 5A  FIG. 5B
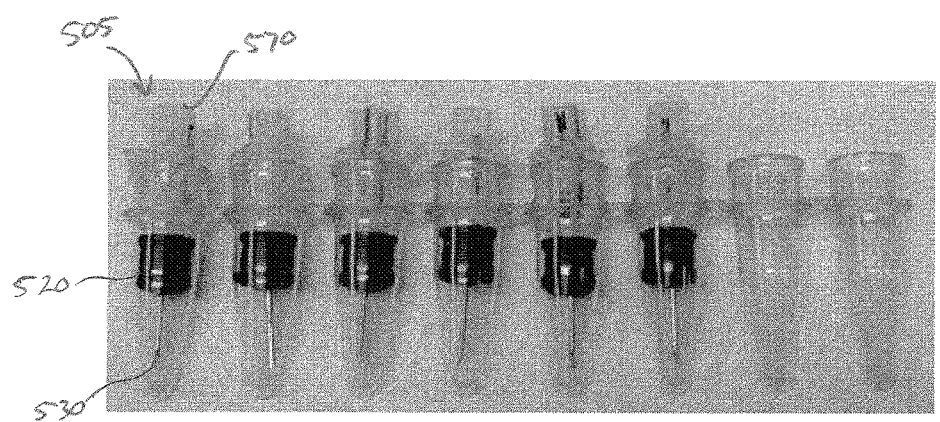
FIG. 6

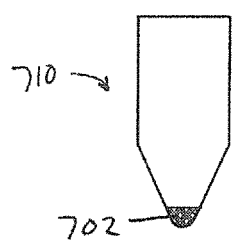
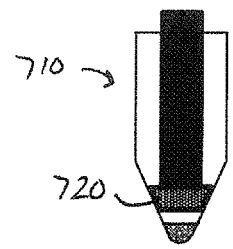
FIG. 10A  FIG. 10B
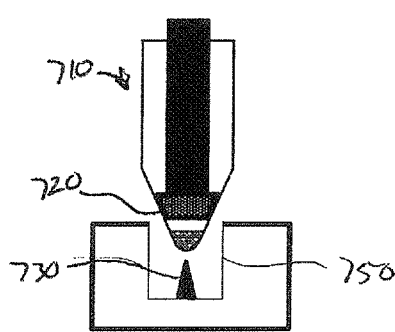
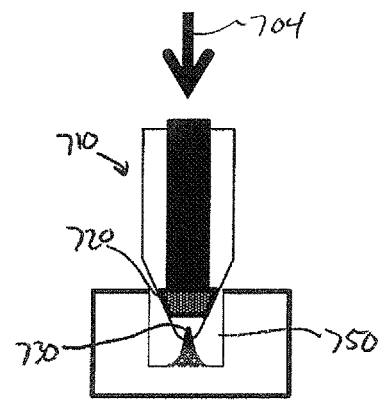
FIG. 10C  FIG. 10D

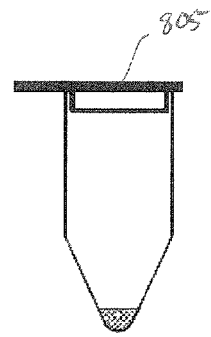
FIG. 11A
FIG. 11B
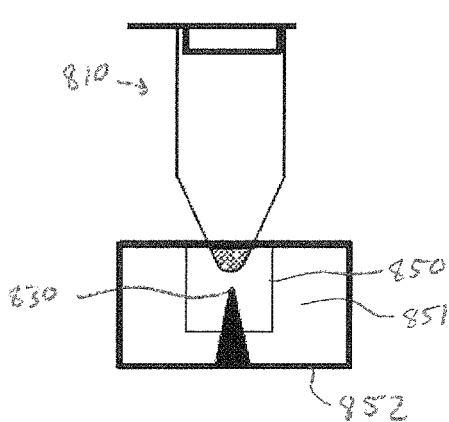
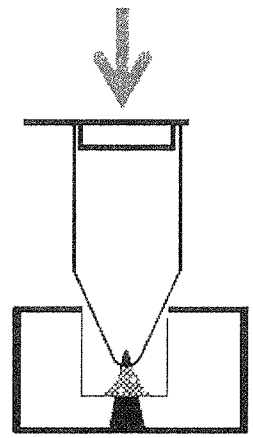
FIG. 11C
FIG. 11D

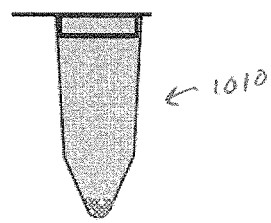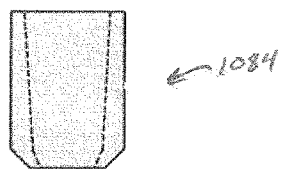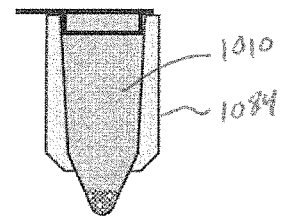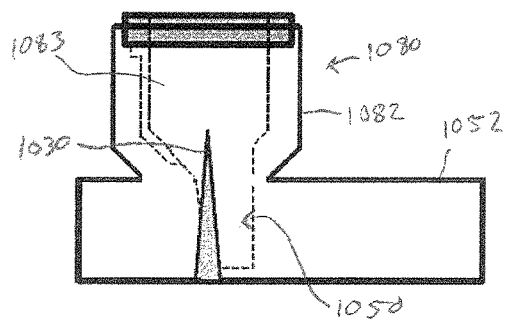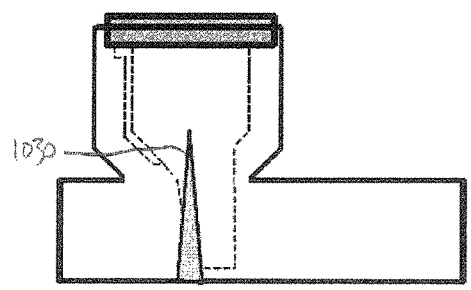
FIG. 13A          FIG. 13B
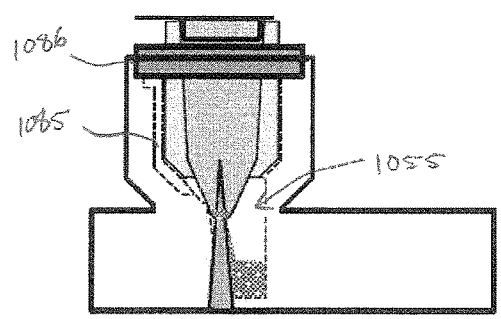
FIG. 13C

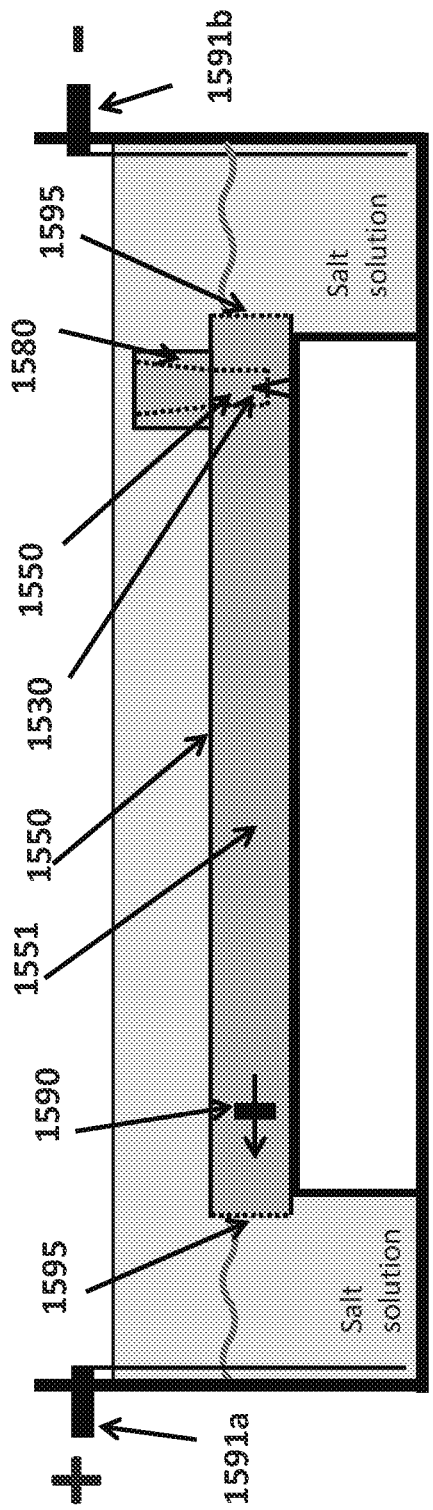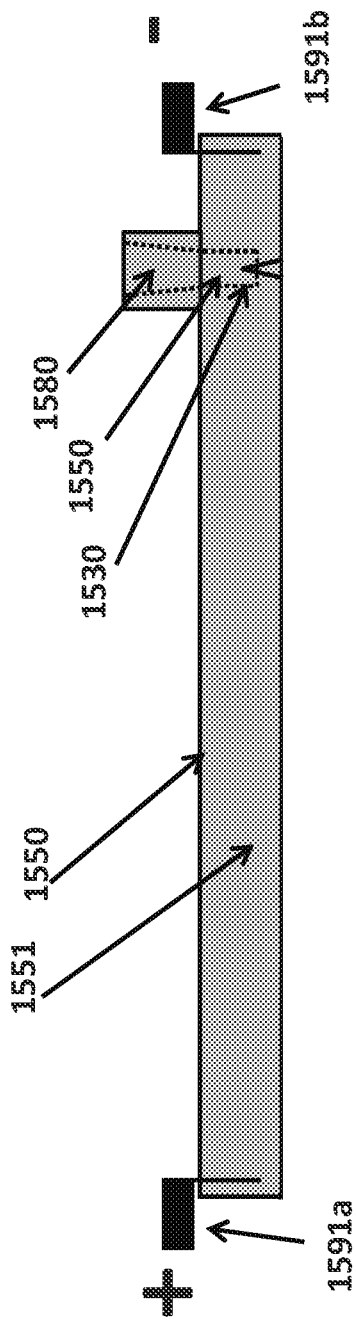
Fig. 15A
Fig. 15B

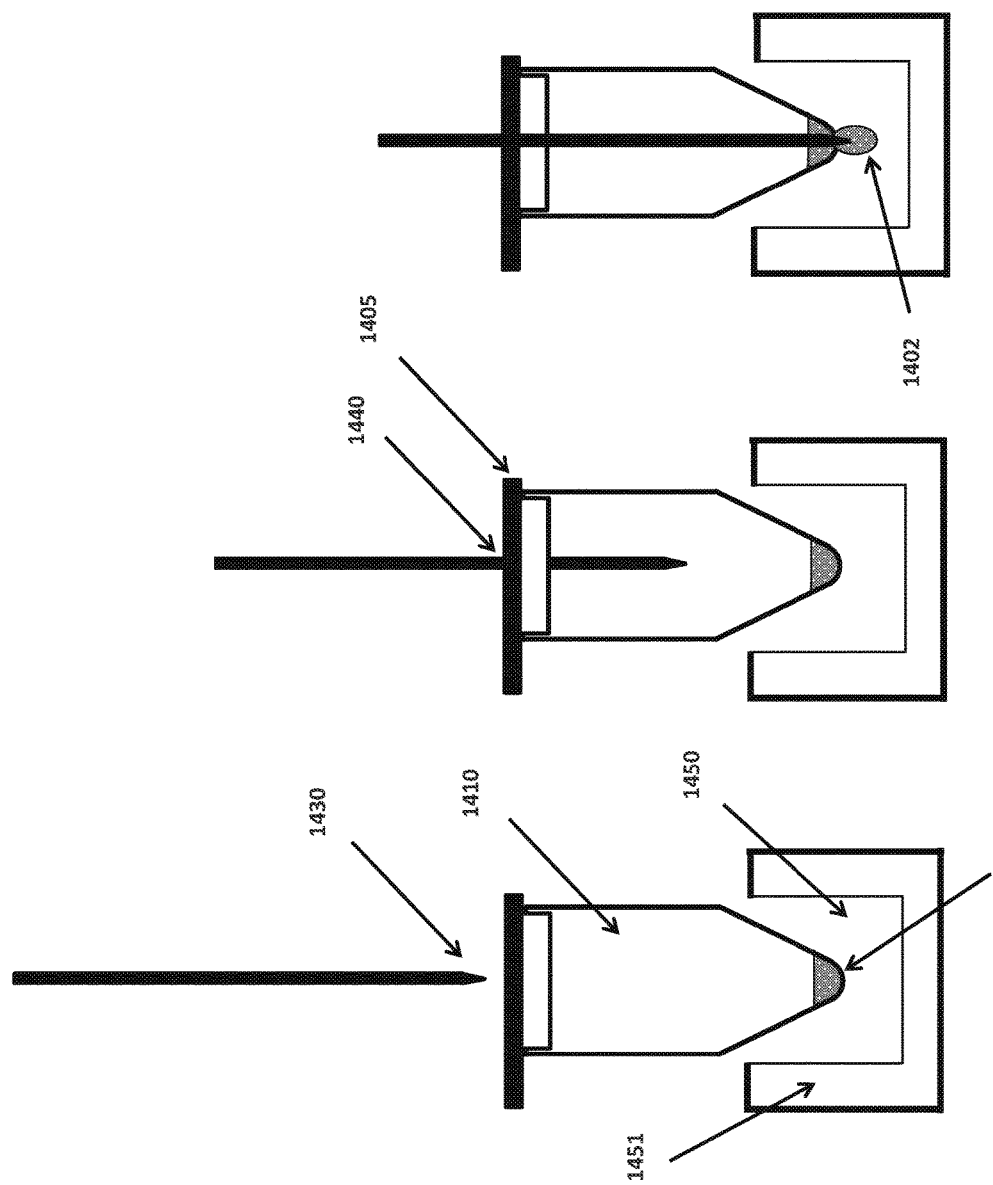

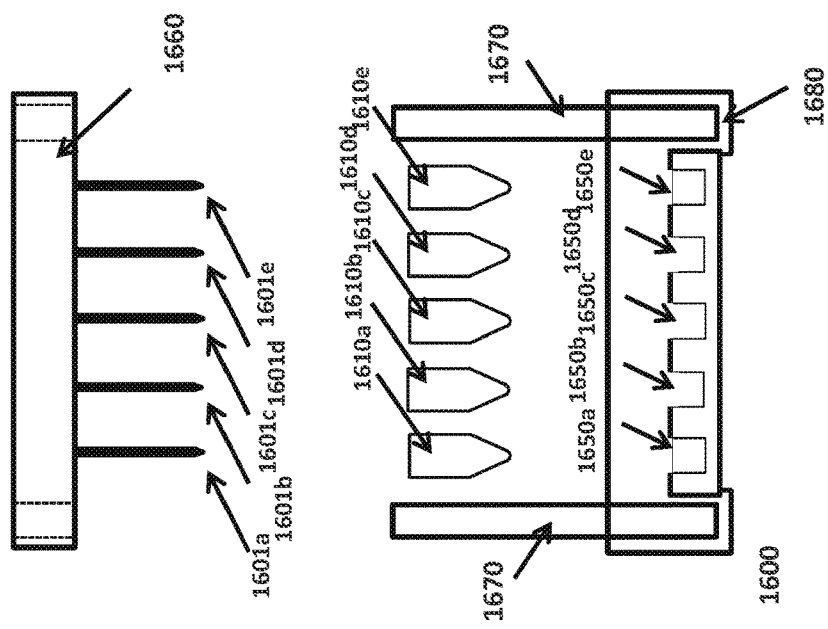

LIQUID DISPENSING DEVICE

FIELD OF THE INVENTION

The present invention relates generally to laboratory devices and associated methods. Accordingly, the present invention involves the mechanical arts field.

BACKGROUND OF THE INVENTION

It is common practice in molecular biology laboratories to load the products of a nucleic acid amplification reaction, such as a polymerase chain reaction (PCR), directly into the wells of an electrophoresis gel in order to resolve the resulting DNA fragments. This is traditionally accomplished by pipetting the reaction mixture from the vial or tube in which the reaction was performed into the open well of the gel. Due to the enormous degree of amplification common in these types of reactions, a tiny fraction of the resulting amplification products can contaminate a subsequent amplification reaction such that the resulting nucleic acids will result from the contaminant and not the intended input sample. Loading amplification products into a gel and the subsequent handling of that gel represent likely sources of laboratory contamination.

SUMMARY OF THE INVENTION

While some attempts have been made to decrease contamination risk, the traditional use of an open end pipette tip to transfer reaction products or other chemical constituents from a container, vial or test tube presents a significant contamination risk to the surrounding laboratory environment. The present inventors have recognized a need for a device that can facilitate transfer of the contents of vials or tubes, particularly PCR tubes, directly into wells of the electrophoresis gel or other transfer target within a completely enclosed system. In one aspect present invention, following electrophoresis and visualization, the gel and the liquid container and dispensing system can be discarded intact, thus keeping the amplification products sealed.

Accordingly, the present invention provides in one embodiment, a liquid dispensing device for a vial or container, and associated systems and methods thereof. In such embodiment, the device may include: 1) a penetrating tip or blade situated such that it pierces the vial or container to create an opening or a path allowing the liquid contents to exit the vial or container directly into wells of the gel or other transfer target; 2) a mechanism to generate force to move said liquid contents, including moving all or part of said liquid contents out of the container or vial; and 3) a substantially or completely enclosed system such that the act of liquid transfer does not create a contamination risk to the surrounding environment.

In one aspect, for example, the penetrating tip includes a recess configured to provide or create at least a portion of a fluid passageway to facilitate dispensing the liquid from the container to the receptacle. The recess can comprise a groove, channel, slot, tunnel, conduit or any other suitable feature or configuration for facilitating passage of fluid through an opening in the container or vial while the penetrating tip is disposed or located in the opening.

In another aspect, for example, such a liquid dispensing device may include a plunger configured to be disposed within a vial and operable to form a seal about an inner surface of the vial. The liquid dispensing device can also include a penetrating tip configured to penetrate a bottom of the vial. The plunger and the inner surface can define a volume in the vial that initially includes a liquid. In addition, the plunger can be movable to cause the penetrating tip to create an opening in the bottom of the vial and to cause the plunger to reduce the volume and dispense the liquid from the vial through the opening. In one aspect the penetrating tip can be coupled to the plunger. In another aspect, the penetrating tip can be located outside the vial.

In another aspect, for example, such a liquid dispensing device may include a penetrating tip or blade located outside the container or vial, such as over a top of the container, and can pierce an entry point in one portion of the container, through the internal space of the container, then pierce an exit point in the bottom of the container and exit the container. If the penetrating tip does not contain a recess at the entry point, it can create an airtight seal at the entry point. If the penetrating tip contains a recess at the exit point, or if the penetrating tip is then withdrawn from the exit point, it can create a passageway for the liquid to exit the container. If positive pressure is generated within the container, the liquid will be dispensed from the container or vial out through the exit point and into the receptacle. The positive pressure can be generated by the volume displaced by the penetrating tip, by squeezing the container, by gravity, centrifugal force, and/or by heating the container.

The present invention also provides a liquid dispensing system. The system can include a container having a liquid disposed therein, a receptacle to receive the liquid, and a penetrating tip disposed over a bottom of the receptacle and configured to penetrate a bottom of the container. Relative movement of the penetrating tip and the container toward one another can be operable to create an opening in the bottom of the container. Liquid can dispense from the container to the receptacle through the opening white the penetrating tip extends through the opening or in some embodiments by withdrawing the penetrating tip.

The present invention further provides a liquid dispensing container support apparatus. The support apparatus can include a support structure and an opening extending through the support structure. The opening can have a top portion and a bottom portion. The top portion can be configured to receive and support a container disposed therein and the bottom portion can be configured to be disposed over a receptacle, such that liquid dispensed from the container passes into the receptacle. In one embodiment, the receptacle is a well of an electrophoresis device. The electrophoresis device can include a housing and a gel disposed within the housing.

To prevent contamination of the surrounding environment, it is desirable that the potential contaminants, such as PCR products or other materials that are the subject of the transfer, remain contained and kept from exposure to an open environment. In the case of an electrophoresis device, it is important that the contaminants remain in the gel matrix or within the housing. In order to do this, power to the electrophoresis device may be removed prior to the point that the contaminants exit the gel matrix and enter the surrounding buffer, which is often open to the laboratory environment, Alternatively, the electrodes or at least the positive electrode may be sealed inside the electrophoresis device. Alternatively, a membrane that allows passage of ions but not the contaminants may be used to seal the electrophoresis device from the surrounding buffer.

There has thus been outlined, rather broadly, various features of the invention so that the detailed description thereof that follows may be better understood, and so that the present contribution to the art may be better appreciated.

Other features of the present invention will become clearer from the following detailed description of the invention, taken with the accompanying claims, or may be learned by the practice of the invention.

BRIEF DESCRIPTION OF THE DRAWINGS

FIGS. 3A and 3B are schematic views of a penetrating tip, in accordance with an example of the present disclosure.

FIGS. 4A and 4B are schematic views of a penetrating tip, in accordance with another example of the present disclosure.

FIG. 5A is a schematic view of a liquid container and dispensing system, in accordance with another example of the present disclosure.

FIG. 5B is a schematic view of a liquid container and dispensing system, in accordance with yet another example of the present disclosure.

FIG. 6 illustrates a cover for sealing a top opening of a container and dispensing a liquid from a bottom of the container, in accordance with an example of the present disclosure.

FIGS. 10A-10D illustrate the liquid container and dispensing system of FIG. 9 in use, in accordance with an example of the present disclosure.

FIGS. 11A-11D illustrate a liquid dispensing system in accordance with example of the present disclosure.

FIGS. 13A-13C illustrate a liquid dispensing system in accordance with yet another example of the present disclosure.

FIG. 15A-15B illustrate a gel electrophoresis device in accordance with an example of the present disclosure.

FIGS. 16A-16C illustrate a liquid dispensing system in accordance with yet another example of the present disclosure.

FIGS. 17A-17C illustrate a liquid dispensing system in accordance with yet another example of the present disclosure.

DETAILED DESCRIPTION OF THE INVENTION

Definitions

Figure 1A:
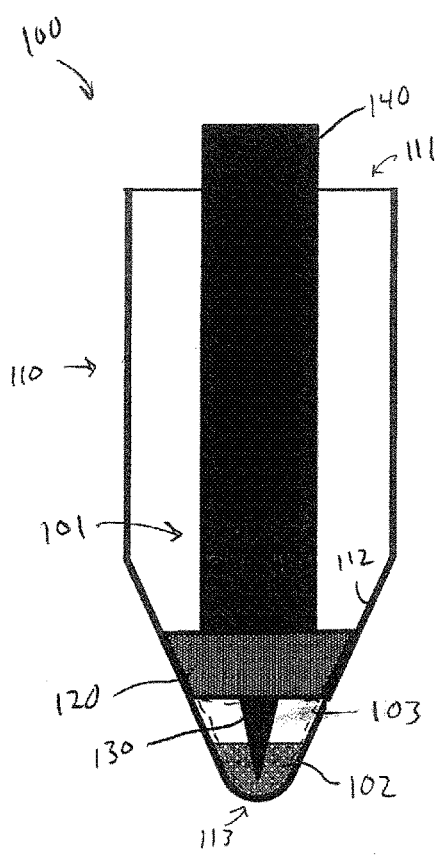
FIGS. 1A and 1B are schematic views of a liquid container and dispensing system, in accordance with an example of the present disclosure.

In describing and claiming the present invention, the following terminology will be used in accordance with the definitions set forth below.

As used herein, the term "container" refers to any form of container for a liquid, such as a vial or other such laboratory container.

The singular forms "a," "an," and, "the" include plural referents unless the context clearly dictates otherwise. Thus, for example, reference to "a liquid dispensing device" includes reference to one or more of such liquid dispensing devices, and reference to "the container" includes reference to one or more of such containers.

As used herein "container" is a vessel that can hold a liquid or material to be transferred. In some embodiments, a container can completely enclose the liquid or material being held.

As used herein, a "vial" is a type of container that is frequently used in a laboratory setting. Often a vial has a top opening through which liquid or other material enters and a lid to close the top opening. Additionally, a vial often has a tapered bottom end. A variety of vials, including those for specific use in PCR are known to those in the art.

As used herein "potential contaminant" can refer to the liquid or material held in a vial or container which is to be transferred to a receptacle, such as a well of an electrophoresis device or gel. Reference to a liquid or material as a "contaminant" or "potential contaminant" should not necessarily connote a substance that is hazardous, toxic, or otherwise dangerous. Rather, such a reference means only that such material is desired to be kept from entering certain areas and is desired to be kept within certain other areas.

As used herein, the term "about" is used to provide flexibility to a numerical range endpoint by providing that a given value may be "a little above" or "a little below" the endpoint.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely tacked particles. In other words, a composition that is "substantially free of" an ingredient or element may still actually contain such item as long as there is no measurable effect thereof.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

The Invention

Figure 1B:
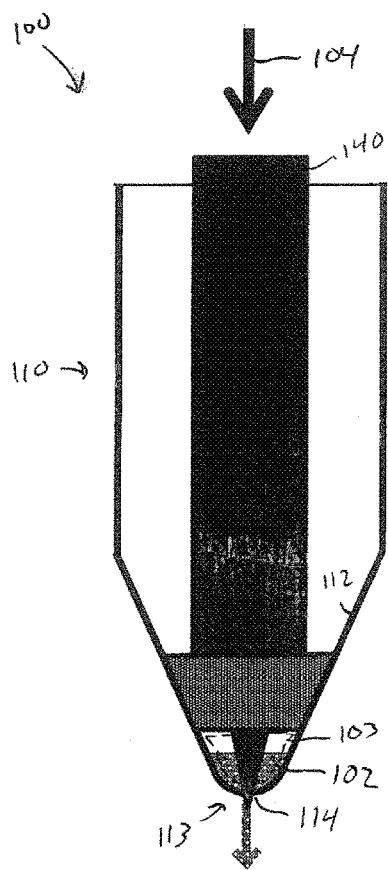

The present invention relates to a liquid dispensing device for a vial or container, and associated systems and methods. With reference to FIGS. 1A and 1B, illustrated is a liquid container and dispensing system 100, which can include such a liquid dispensing device 101. For example, the system 100 can include a container 110 or vial, such as a laboratory tube, having a top opening 111, an inner surface 112, and a bottom 113. As shown in FIG. 1A, a liquid 102 can be disposed in the container. The liquid dispensing device can include a plunger 120 configured to be disposed within the container or vial. The plunger can be operable to form a seal about the inner surface of the container or vial. In one aspect, the plunger can comprise a compliant material, such as an elastomer, to facilitate forming a seal when in contact with the inner surface. The liquid dispensing device can also include a penetrating tip 130 configured to penetrate the bottom of the container or vial. In one aspect, the penetrating tip can be associated with the plunger. The plunger and the inner surface can define a volume 103 in the container or vial that initially includes the liquid, as shown in FIG. 1A. In one aspect, the volume can also initially include the penetrating tip. One benefit of the devices and systems described herein is that the portion of the volume above the liquid, which can contain air, is minimized compared to standard tube caps, thus minimizing evaporation from an amplification reaction.

In one aspect, the plunger can be movable, such as in direction 104 as shown in FIG. 1B, to cause the penetrating tip to create an opening 114 in the bottom of the container or vial and to cause the plunger to reduce the volume and dispense the liquid from the container or vial through the opening. Thus, the pressure created by the downward movement of the plunger can force the liquid out of the container or vial through the hole created by the penetrating tip. In one aspect, the liquid dispensing device can include an extension portion 140 coupled to the plunger. The extension portion can be configured to extend from the container or vial to provide a user interface for causing movement of the plunger. As shown, the extension portion can also be coupled to the penetrating tip to cause movement of the penetrating tip, as well. In another aspect, the extension portion may not be coupled to the plunger, but may be merely brought into contact with the plunger by a user and force applied to the plunger with the extension portion in order to advance the plunger.

The penetrating tip can comprise any suitable configuration for creating one or more openings in the container or vial. For example, as illustrated, the penetrating tip can comprise a pointed or sharp end to pierce, puncture, cut, and/or, slice the container. In one aspect, the penetrating tip can comprise a blade or multiple blades that create a linear or star shaped opening. In another aspect, the penetrating tip can comprise a tapered or wedge-like configuration to expand or enlarge an initial piercing or penetration in the container to form an opening of a suitable size for facilitating the passage of liquid through the opening and out of the container. In another aspect, the bottom of the container or vial can be configured to facilitate formation of the opening, such as by having a thin or weakened area configured to easily be pierced, penetrated, or ruptured by the penetrating tip. In a particular aspect, the container can include a thin membrane, such as a foil, disposed over a preexisting hole in the container. Thus, the penetrating tip can penetrate the membrane to form an opening through the membrane and preexisting hole to facilitate removal or draining of the liquid from the container.

Figures 2A, 2B, 2C:
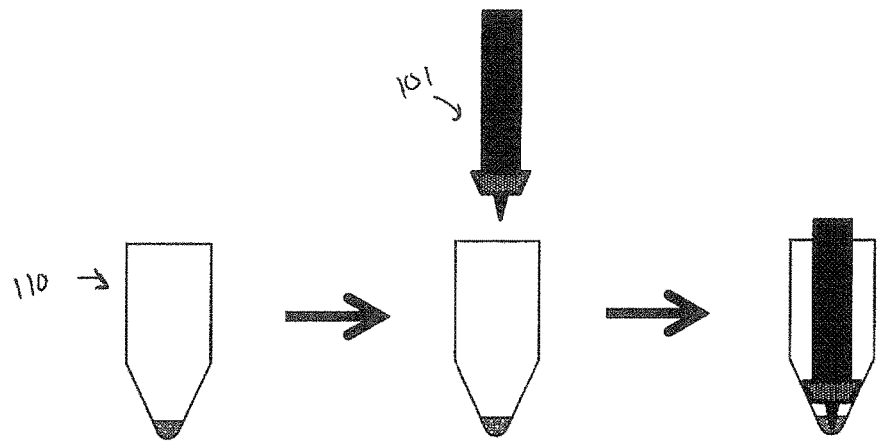
FIGS. 2A-2F illustrate a liquid dispensing device of the system of FIGS. 1A and 1B in use.
Figures 2D, 2E, 2F:
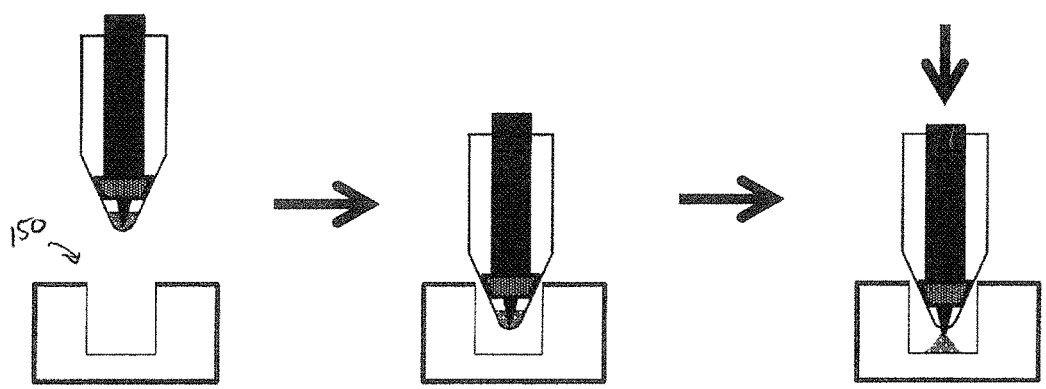

FIGS. 2A-2F illustrate the dispensing device 101, in use. For example, as shown in FIG. 2A, a liquid 102 can be disposed in the container 110 or vial. As shown in FIGS. 2B and 2C, the dispensing device 101 can then be disposed in the container. The container, liquid, and the liquid dispensing device can then be disposed over a receptacle 150 for the liquid, such as a container, plate, or a well in an electrophoresis gel, as shown in FIGS. 2D and 2E. Once properly positioned, the plunger and the penetrating tip can be moved to cause the penetrating tip to create an opening in the bottom of the container and to cause the plunger to reduce the volume and dispense the liquid from the container through the opening and directly on or into the receptacle for the liquid. It should be recognized that the devices and systems disclosed herein can be used to transfer any type of liquid contents from one container, such as a plastic tube or vial, to any other suitable container.

FIGS. 3A and 3B illustrate a penetrating tip 230 in accordance with an example of the present disclosure. In this case, the penetrating tip includes a recess 231 configured to provide a fluid passageway 232 to facilitate, dispensing the liquid from the container to the receptacle with the penetrating tip disposed in the bottom opening or extending through the opening. The recess can comprise a groove, channel, slot, or any other suitable feature or configuration for facilitating passage of fluid through an opening while the penetrating tip is disposed or located in the opening.

FIGS. 4A and 4B illustrate a penetrating tip 330 in accordance with another example of the present disclosure. As with the penetrating tip 230 of FIGS. 3A and 3b, the penetrating tip 330 includes a recess 331 configured to provide a fluid passageway 332 to facilitate dispensing the liquid from the container with the penetrating tip disposed in the bottom opening. In this case, the recess can comprise a groove, channel, or slot, formed on opposite sides or around a circumference of the penetrating tip. The configuration of the penetrating tip 330 and the recess 331 also facilitates blocking or plugging the opening with further movement of the penetrating tip into the opening. This can permit a user to regulate flow of liquid from the container by moving the penetrating tip relative to the opening once the opening has been formed.

FIGS. 5A and 5B illustrate liquid container and dispensing systems in accordance with additional examples of the present disclosure. As shown in FIG. 5A, a liquid container and dispensing system 400a can include a support or guide structure 460a for an extension portion 440a of a dispensing device 401a. The support or guide structure can be configured to maintain the extension portion in a proper alignment relative to a container 410a during movement of the penetrating tip and the plunger to facilitate proper function of the penetrating tip and the plunger, as disclosed herein. In one aspect, the support or guide structure can be associated with the container and can be configured to facilitate sliding movement of the extension portion relative to the support or guide structure. In another aspect, the support or guide structure can be associated with the extension portion and can be configured to facilitate sliding movement of the container relative to the support or guide structure.

As shown in FIG. 5B, a liquid container and dispensing system 400b can include a plunger 420b configured to function as a support or guide stuck/re for a dispensing device 401a. For example, the plunger can be configured to interface with a cylindrical upper portion of a container 410b, as opposed to a conical or tapered lower portion of the container. The plunger is also configured to utilize one or more O-rings or the like to form a seal with the upper portion of the container. In addition, this example illustrates that the plunger may facilitate dispensing liquid from the container without contacting the liquid.

In one aspect, the plunger 420b includes a penetrating tip 430b that has a recess 431b configured to provide a fluid passageway to facilitate dispensing the liquid from the container with the penetrating tip disposed in the bottom opening. The recess can be oriented substantially parallel to a penetration direction of the penetrating tip.

FIG. 6 illustrates another aspect of the present disclosure. In this figure, a cover 505 is illustrated for sealing a top opening of a container and dispensing a liquid from a bottom of the container. Similar to other embodiments disclosed hereinabove, the cover 505 can include a plunger 520 and a penetrating tip 530. In other words, the cover can include a liquid dispensing device as disclosed herein. In addition, the cover can include a cap 570 coupled to the plunger and the penetrating tip and configured to extend from the container proximate the top opening to provide a user interface for causing movement of the plunger and the penetrating tip. In one aspect, the cap can also provide some form of barrier to protect or shield the interior of the container above the plunger. In another aspect, the cap can be configured to fit within the container and move, at least partially, inside the container when moving the plunger and the penetrating tip.

Additionally, FIG. 6 illustrates multiple caps coupled together in a "strip" configuration. This configuration can be convenient when using the caps with a series of containers or vials coupled together in a strip configuration, as is common for ease of handling certain vials with certain laboratory equipment.

Figure 7A:
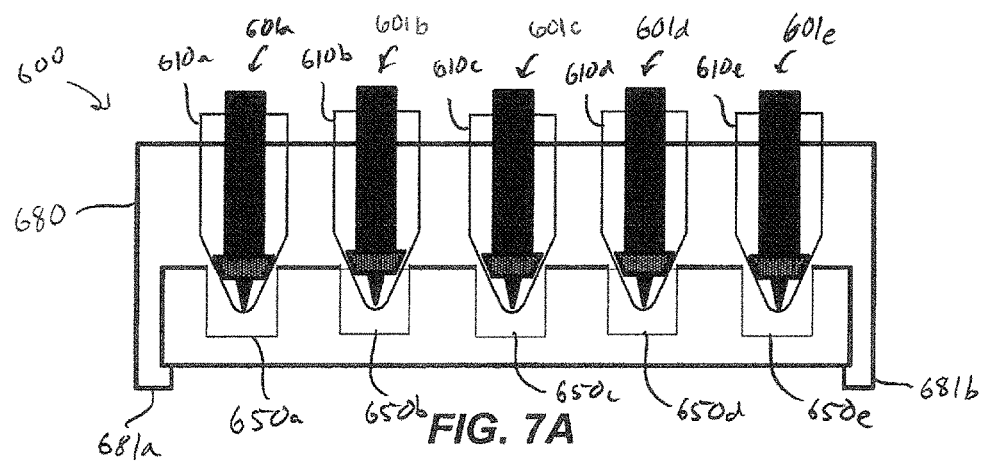
FIGS. 7A-7C illustrate several views of a liquid container and dispensing system, in accordance with another example of the present disclosure.
Figure 7B:
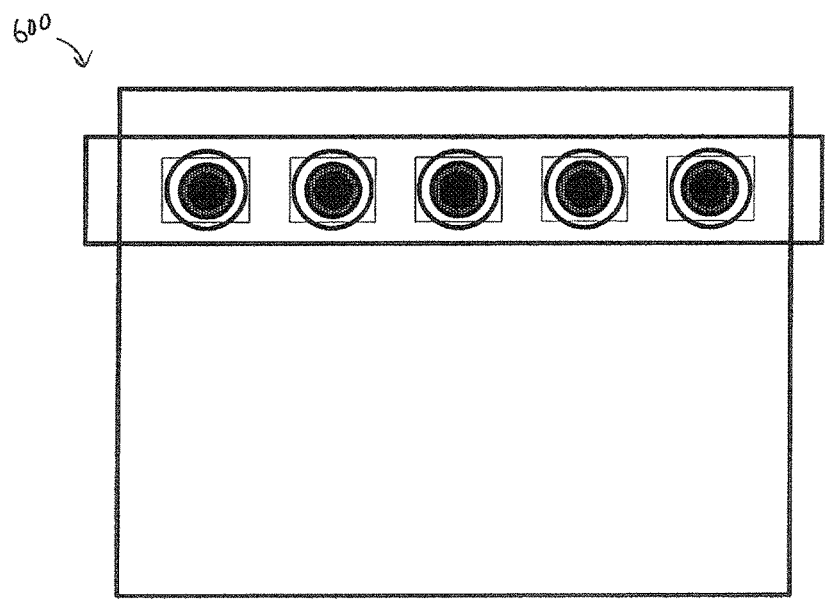
Figure 7C:
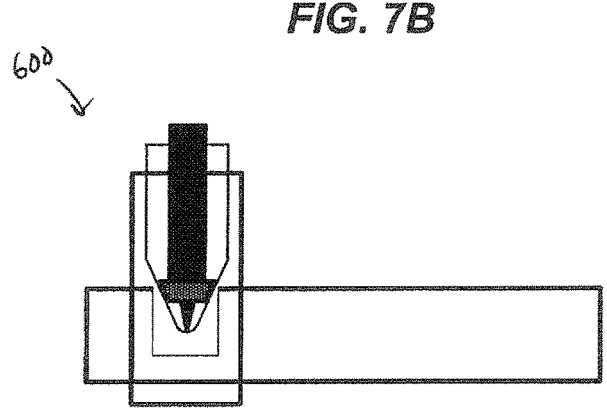

FIGS. 7A-7C illustrate several views of a liquid container and dispensing system 600 in accordance with another example of the present disclosure. The system can include one or more containers 610a-e or vials and associated liquid dispensing devices 601a-e, respectively, as disclosed herein. In addition, the system can include a support apparatus or manifold 680 configured to hold or support multiple containers in place, such as above receptacles 650a-e. In one aspect, the manifold can include a clip 681a, 681b to secure the manifold to the receptacles or a structure supporting the receptacles. The manifold and the clips can be configured to provide stable support for the containers about the receptacles as the liquid dispensing devices are operated.

Figure 8A:
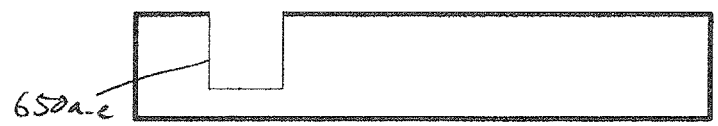
FIGS. 8A-8D illustrate the liquid container and dispensing system of FIGS. 7A-7C in use, in accordance with an example of the present disclosure.
Figure 8B:
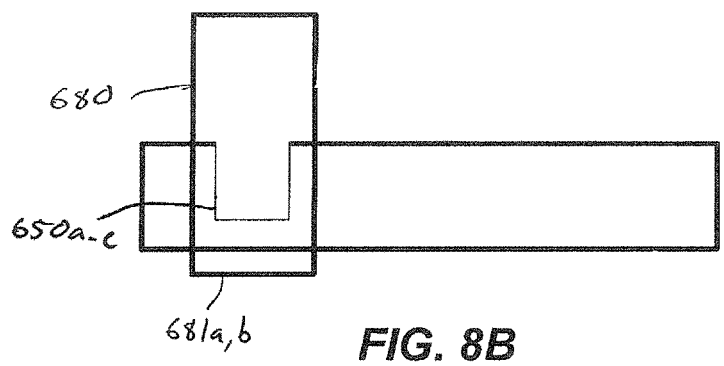
Figure 8C:
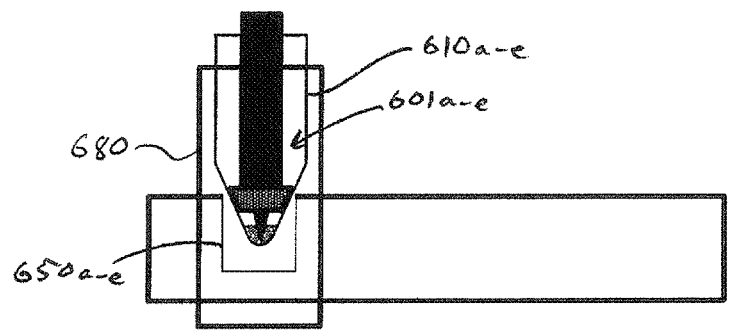
Figure 8D:
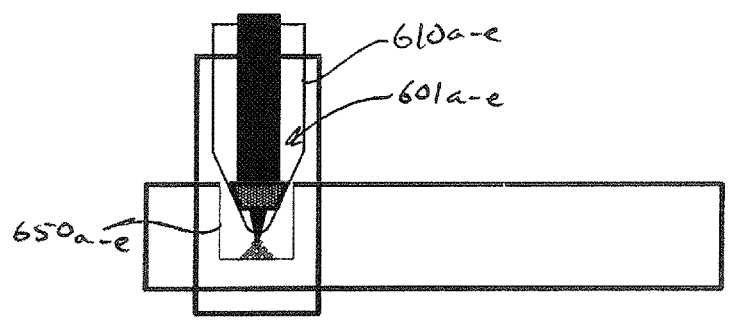

FIGS. 8A-8D illustrate one example of the system 600 in use. For example, as shown in FIG. 8A, the receptacles 650a-e can be prepared to receive a liquid. The manifold 680 can then be located relative to the receptacles, as shown in FIG. 8B, to properly position the containers over the receptacles, such as by utilizing the clips 681a, 681b. As shown in FIG. 8C, the containers 610a-e including liquid and liquid dispensing devices 601a-e can be disposed on, and supported by, the manifold 680. The liquid dispensing devices can then be operated to dispense the liquid from the containers, as shown in FIG. 8D. In another aspect, the manifold and receptacles can be manufactured as a single piece.

Figure 9:
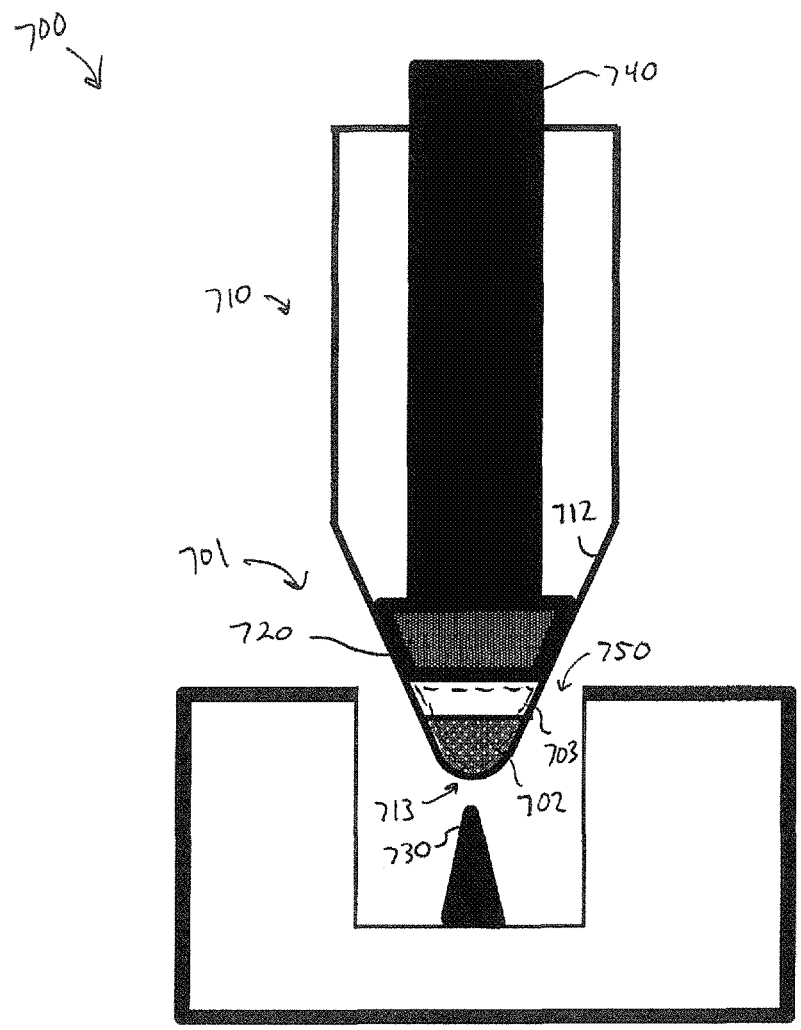
FIG. 9 is a schematic view of a liquid container and dispensing system, in accordance with another example of the present disclosure.

With reference to FIG. 9, illustrated is a liquid container and dispensing system 700, in accordance with another embodiment of the present disclosure. As with other liquid container and dispensing systems disclosed hereinabove, the liquid container and dispensing system 700 can include a container 710 and a liquid dispensing device 701, which includes a plunger 720 and a penetrating tip 730. In this case, prior to creating an opening in a bottom 713 of the container, the penetrating tip is outside a volume 703 defined by the plunger and an inner surface 712 of the container and includes a liquid 702. Here, movement of the plunger acts on the container, such as against the inner surface, to force the container onto the penetrating tip to create the opening. In one aspect, the liquid container and dispensing system 700 can include a receptacle 750 to receive the liquid from the container. In a particular aspect, the penetrating tip can be disposed in the receptacle, as shown in the figure. The liquid dispensing device can also include an extension portion 740 coupled to the plunger and configured to extend from the container to provide a user interface for causing movement of the plunger. In another aspect, a separate force or forces can be applied to either the container or the receptacle to force the container onto the penetrating tip to create the opening.

FIGS. 10A-10D illustrate one example of the system 700 in use. For example, as shown in FIG. 10A, the liquid 702 can be disposed in the container 710. The plunger 720 can then be disposed in the container, as shown in FIG. 10B. As shown in FIG. 10C, the container 710 including the liquid and the plunger can be over the penetrating tip 730 in preparation to creating the opening. In this case, the penetrating tip is disposed outside the container, in the receptacle 750. In this position, a downward force 704 can be applied to the plunger, as shown in FIG. 10D, which reduces the volume, creating a positive pressure inside the container. The downward force on the plunger also drives the container onto the penetrating tip to create an opening in the bottom of the container, thus dispensing the liquid from the container and into the receptacle. In other words, relative movement of the penetrating tip and the container toward one another can be operable to create the opening in the bottom of the container.

In a related embodiment, a method of dispensing a liquid from a vial containing the liquid in accordance with the principles herein is disclosed. The method comprises forming an opening in a bottom of the vial. In some aspects, the opening can be formed from inside the vial. In other aspects, the opening can be created or formed from outside the vial. Additionally, the method comprises dispensing the liquid from the vial through the opening. In one aspect of the method, forming an opening comprises at least one of penetrating, piercing, puncturing, and rupturing a bottom portion of the vial. It is noted that no specific order is required in this method, though generally in one embodiment, these method steps can be carried out sequentially.

In addition, FIGS. 11A-11D illustrate another aspect of the present disclosure. As with the system 700 illustrated in FIGS. 9-10D, FIGS. 11A-11D illustrate use of a liquid dispensing system that includes a container 810 and a liquid 802 disposed in the container (FIG. 11A), and a receptacle 850 to receive the liquid, with a penetrating tip 830 located outside the container (FIG. 11C), such as over a bottom of the receptacle. In one aspect, the receptacle can comprise a gel 851, such as an electrophoresis and the penetrating tip can extend through the gel. In another aspect, the penetrating tip can be supported by a housing 852 that contains the receptacle or gel. In addition, the liquid can be dispensed from the container by positive pressure within the container. For example, absent a plunger as is included in some examples disclosed herein, the positive pressure can be generated by disposing a cover 805 or lid on the container (FIG. 11B), by squeezing the container, and/or by heating the container. In another example, the liquid can be dispensed from the container by centrifugal force or by gravity.

Figure 12:
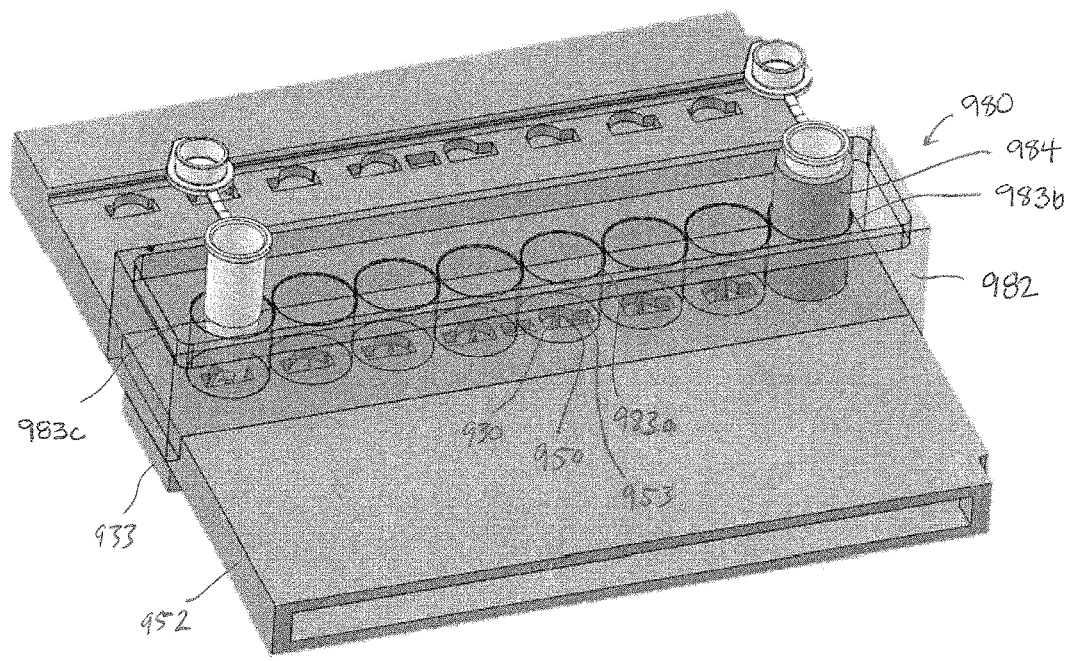
FIG. 12 illustrates a liquid dispensing system in accordance with another example of the present disclosure.

Additional aspects of a liquid dispensing system in accordance with the present disclosure are illustrated in FIG. 12. For example, a support apparatus 980 for a liquid dispensing container is shown. The support apparatus can include a support structure 982 and an opening, such as multiple openings 983a-c, extending through the support structure. The support structure can be removably attachable to the housing, permanently attached to the housing, or contiguous with the housing. A top portion of the opening can be configured to support a container and a bottom portion of the opening can be configured to be disposed over a receptacle, such as receptacle 950, such that liquid dispensed from the container passes into the receptacle. In one aspect, the opening 983b can be configured to interface with a sleeve 984 for the container. In another aspect, the opening 983c can be configured to interface directly with a container. In either case, a seal can be formed between the container and the opening to prevent or minimize contamination, which is discussed further hereinafter with regard to additional examples of the present disclosure.

As shown in FIG. 12, the support structure 982 can be configured to interface with a housing 952, which can be an injection molded casing for gel that forms the receptacle 950. In one aspect, the support structure can form a seal with the housing to prevent or minimize contamination. The housing can include an opening 953 to provide access to the receptacle from a top side of the housing, such that liquid dispensed from a container can flow into the receptacle. In addition, the housing can be configured to receive a penetrating tip 930 from a bottom side of the housing, which can extend into the receptacle. The penetrating tip can be coupled to a backing member 933 and can extend through the housing and through a bottom of the gel receptacle. The backing member can also form a seal with the housing to prevent or minimize contamination. In one aspect, a plurality of openings in the support structure of the support apparatus can be spaced apart to correspond with a plurality of receptacles to facilitate dispensing liquid from a plurality of containers to the plurality of receptacles. In this case, such a support apparatus 980 may be referred to as a manifold. In another aspect, a plurality of penetrating tips can be coupled to a common backing member 933 and spaced apart to correspond with the plurality of receptacles to form a rack of penetrating tips that can facilitate dispensing liquid from a plurality of containers to the plurality of receptacles. In another aspect, the housing and manifold, housing and pin rack of penetrating tips, or all three members can be formed as a single piece by a process such as injection molding.

In use, the support apparatus or manifold 980 can be disposed on the housing 952 such that the bottom portions of the openings are over the receptacles. A rack of penetrating tips can also be disposed in the receptacles by extending the penetrating tips through the bottom of the housing. Individual containers or a strip of multiple containers can be placed in respective openings of the support apparatus. A downward force can be applied to the containers, causing the penetrating tips to create openings in the bottoms of the containers and dispense liquid from the containers to the receptacles. Following electrophoresis and visualization, the entire assembly of the housing, gel, manifold, rack of penetrating tips, and containers can be discarded, intact, to keep amplification products sealed.

FIGS. 13A-13C illustrate a liquid dispensing system in accordance with another embodiment of the present disclosure. As with some other examples disclosed herein, the system includes a support apparatus or manifold 1080 having an opening 1083 disposed over a receptacle 1050, and a penetrating tip 1030 located, initially, outside a container 1010, such as extending up through a bottom of the receptacle. In this case, a support structure 1082 of the support apparatus 1080 is integrally formed with a housing 1052 for the receptacle. In addition, a sleeve 1084 can be configured to interface with the container and a top portion of the opening of the support apparatus.

In one aspect, the sleeve 1084 can facilitate reliable puncture of the container 1010 and transfer of the liquid to the receptacle 1050. For example, the sleeve can ensure that the center of bottom of the container aligns with the penetrating tip. In some embodiments, the outer walls of the container are tapered or non-parallel, and therefore are not parallel to the desired direction of movement to cause the penetrating tip to penetrate the bottom of the container. In such cases, the walls of the container may be inadequate to guide movement of the container onto the penetrating tip. The inside of the sleeve can therefore be configured to conform to the container shape and the outside of the sleeve can be configured to be parallel to the desired direction of movement of the container onto the penetrating tip. At least the upper portion of the opening 1083 can be configured with an interface surface that is parallel to the direction of movement of the container and configured to direct a desired portion of the bottom of the container into contact with the penetrating tip. For example, the interface surface can be configured to be concentric with the container, the sleeve, and/or the penetrating tip. In addition, the interface surface can be sized to receive the sleeve in a sliding engagement or interface. The sleeve can therefore function as a carrier for the container.

In use, the container 1010 can be inserted into the sleeve 1084, and the sleeve can be inserted into the opening 1083 of the support apparatus or manifold 1080, where a desired penetration location of the bottom of the container can be aligned with the penetrating tip 1030. A downward force applied to the container can then cause the penetrating tip to create an opening in the bottom of the container to facilitate dispensing the liquid from the container and into the receptacle 1050.

In one aspect, the support apparatus can include a vent channel 1085 to facilitate the escape of gas or pressure that may build up in the receptacle 1050 and/or the sealed space 1055 when the container and sleeve are disposed in the opening of the support apparatus. For example, a top seal or filter ring 1086 disposed about the upper portion of the opening can be configured to release gas pressure escaping via the vent path, and still provide a sealed space within the support apparatus and the housing. The top seal or fitter ring can also function to retain the container and/or prevent leakage of contaminants into and/or out of the receptacle and/or the sealed space, such as by capturing potential contaminants (i.e., PCR products in the liquid).

In one aspect, the sleeve 1084 can be configured to form a seal between the container and the top portion of the opening and define, at least in part, a sealed space 1055 for dispensing liquid from the container to the receptacle (FIG. 13C). In another aspect, the sleeve 1084 can be configured as an adapter to facilitate use of the container 1010 in the opening 1083 of the support apparatus 1080. Thus, for example, sleeves can be provided having a variety of inner dimensions to interface with and accommodate different sized containers to facilitate use of various sized and shaped containers in the same opening or same sized opening of the support apparatus.

Figure 14:
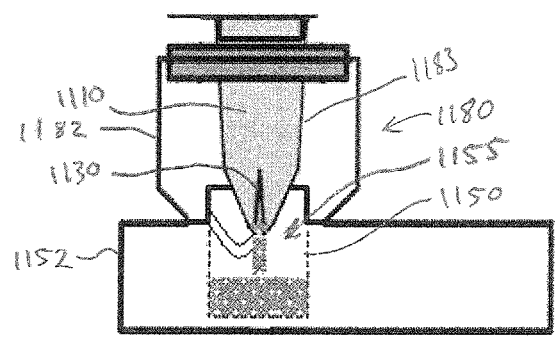
FIG. 14 illustrates a liquid dispensing system in accordance with still another example of the present disclosure.

FIG. 14 illustrates a liquid dispensing system in accordance with yet another example of the present disclosure. This system is similar in many respects to the system illustrated in FIGS. 13A-13C. For example, the system of FIG. 14 includes a support apparatus or manifold 1180 having an opening 1183 disposed over a receptacle 1150 and a penetrating tip 1130 located, initially, outside a container 1110. In this case, the top portion of the opening is configured to directly interface with the container. Thus, the top portion of the opening can be configured to form a seal with the container and define, at least in part, a sealed space 1155 for dispensing liquid from the container to the receptacle. In addition, the penetrating tip extends laterally from a support structure 1182 of the support apparatus to be disposed over the bottom of the receptacle, instead of extending through the bottom of the receptacle. Thus, in one aspect, the support apparatus can include the penetrating tip. Alternately, the penetrating tip can extend laterally from a side of the receptacle or laterally from the housing 1152.

FIGS. 15A-15B illustrate gel electrophoresis devices including one aspect of the present disclosure including a manifold 1580, receptacle 1550, and penetrating device 1530. The gel electrophoresis device can include a housing 1252 and a get 1251 disposed in the housing as well as electrically conductive members 1291a, 1291b disposed at or near the opposite ends of the housing. The gel can comprise any standard or typical gel for electrophoresis use, such as agarose. In order to prevent the potentially contaminating molecules originally present in the liquid within the container from contaminating the surrounding environment, it is desirable that they remained confined within the electrophoresis device. This can be accomplished by removing power to the electrophoresis device prior to the point that the potential contaminating molecules 1590 exit the electrophoresis device. However, since the above mentioned removal of power can be an error prone process, an alternative solution is to contain the potential contaminating molecules within the electrophoresis device. Such containment can be accomplished using a membrane 1595 that allows smaller ions such as salt molecules to pass while retaining larger molecules such as DNA strands. It is also possible to place the electrodes within the electrophoresis device as shown in FIG. 15B.

In addition, FIGS. 16A-16C illustrate another embodiment of the present disclosure. As with the system 700 illustrated in FIGS. 9-10D, FIGS. 16A-16C illustrate use of a liquid dispensing system that includes a container 1410 and a liquid 1402 disposed in the container (FIG. 16A), and a receptacle 1450 to receive the liquid. In one aspect, the receptacle can comprise a gel 1451, such as an electrophoresis gel. A penetrating tip 1430, located outside the container, such as over a top of the container, can pierce an entry point 1440 in one portion of the container (FIG. 16B), pass through the volume of the container, then pierce and exit point through bottom of the container (FIG. 6C). If the penetrating tip is withdrawn from the exit point, or if the penetrating tip contains a recess, tunnel, or other opening at the exit point, it creates a passageway for the liquid 1402 to exit the container and enter the receptacle 1450. The liquid can be dispensed from the container through this passageway by centrifugal force, or by gravity. An alternative force that can be used to cause the above mentioned movement of liquid is to create positive pressure within the container. For example, if the penetrating tip forms an airtight seal at the entry point 1440, the volume displaced by the penetrating tip will create said positive pressure. The positive pressure can also be generated by disposing a cover 1405 or lid on the container, by squeezing the container, and/or by heating the container.

FIGS. 17A-17C illustrate several views of a liquid container and dispensing system 1600 in accordance with another example of the present disclosure. The system can include one or more containers 1610a-e or vials and associated penetrating tips 1601a-e, respectively, as disclosed herein. In addition, the system can include a support apparatus or manifold 1680 configured to hold or support multiple containers in place, such as above receptacles 1650a-e. The system can include a pin bar 1660 to position the penetrating pins and one or more guide posts 1670 to allow proper guidance of the penetrating pins.

FIGS. 17A-17C also illustrate one example of the system 1600 in use. For example, as shown in FIG. 17A, the receptacles 1650a-e can be prepared to receive a liquid. The manifold 1680 can then be located relative to the receptacles, as shown in FIG. 17B, to properly position the containers over the receptacles. The containers 1610a-e including liquid and liquid dispensing devices 1601a-e can be disposed on, and supported by, the manifold 1680. As shown in FIG. 17C, the liquid dispensing devices can then be operated to penetrate the upper portion of the containers, pressurize the volume within the container, then pierce the bottom of the container to dispense the liquid from the containers into the receptacle.

EXAMPLES

The following examples pertain to further embodiments.

In one embodiment, a liquid dispensing system can comprise a container configured to have a liquid disposed therein, and a liquid dispensing device having a penetrating tip configured to penetrate the container, wherein relative movement of the penetrating tip and the container toward one another is operable to create an opening in a portion of the container, and wherein the liquid dispenses from the container through the opening.

In one embodiment, a liquid dispensing device can further comprise a plunger configured to be disposed within the container and operable to form a seat about an inner surface of the container, wherein the plunger and the inner surface define a volume in the container that initially includes a liquid, and wherein the plunger is movable to cause the penetrating tip to create the opening in the portion of the container and to cause the plunger to reduce the volume and dispense the liquid from the container through the opening.

In one embodiment, the penetrating tip comprises a recess configured to provide a fluid passageway to facilitate dispensing the liquid from the container with the penetrating tip disposed in the opening.

In one embodiment, the penetrating tip is associated with the plunger and the penetrating tip is disposed within the volume prior to creating the opening.

In one embodiment, the liquid dispensing device can further comprise an extension portion coupled to the plunger and configured to extend from the container to provide a user interface for causing movement of the plunger.

In one embodiment, the penetrating tip is outside the volume prior to creating the opening, and wherein movement of the plunger, the container, the penetrating tip, or a combination thereof provides contact between the container and the penetrating tip sufficient to create the opening.

In one embodiment, the liquid dispensing device can further comprise a cap coupled to the plunger and the penetrating tip, wherein the plunger is configured to be disposed within the container through a top opening and the cap is configured to extend from the container proximate the top opening to provide a user interface for causing movement of the plunger and the penetrating tip.

In one embodiment, the penetrating tip comprises a recess configured to provide a fluid passageway to facilitate dispensing the liquid from the container with the penetrating tip disposed in the opening.

In one embodiment, the penetrating tip comprises a recess configured to provide a fluid passageway to facilitate dispensing the liquid from the container with the penetrating tip disposed in the opening.

In one embodiment, the liquid dispensing system can further comprise a receptacle, wherein the penetrating tip is configured to be disposed in the receptacle, and liquid dispenses from the container to the receptacle through the opening.

In one embodiment, the penetrating tip comprises a plurality of penetrating tips, and wherein the plurality of penetrating tips are coupled to a common support member and spaced apart to correspond with a plurality of receptacles to facilitate dispensing liquid from a plurality of containers to the plurality of receptacles.

In one embodiment, the liquid dispenses from the container to the receptacle through the opening while the penetrating tip extends through the opening.

In one embodiment, the liquid dispenses from the container to the receptacle through the opening after the penetrating tip has been withdrawn from the opening.

In one embodiment, the penetrating tip is located outside the container and penetrates the container at least twice.

In one embodiment, the liquid dispensing system can further comprise a pressure generator within the container, selected from movement of the penetrating tip within the container, closing a cap of the container, compressing walls of the container, or heating the container.

In one embodiment, the liquid dispensing system can further comprise a receptacle to receive the liquid from the container, wherein the penetrating tip is disposed in the receptacle.

In one embodiment, the receptacle comprises a well of an electrophoresis gel.

In one embodiment, the liquid dispenses from the container to the receptacle through the opening while the penetrating tip extends through the opening.

In one embodiment, the liquid dispenses from the container to the receptacle through the opening after the penetrating tip has been withdrawn from the opening.

In one embodiment, the penetrating tip is coupled to a support member and extends through a housing for the gel and through a bottom of the receptacle.

In one embodiment, the receptacle comprises a gel and the penetrating tip is disposed above the gel.

In one embodiment, the penetrating tip is supported by a housing for the receptacle.

In one embodiment, the liquid is dispensed from e container by positive pressure within the container.

In one embodiment, the positive pressure is generated by disposing a lid on the container, by squeezing the container, by heating the container, or combinations thereof.

In one embodiment, the liquid is dispensed from the contain by centrifugal force or gravity.

In one embodiment, the liquid is dispensed from the container to the receptacle within a sealed space.

In one embodiment, a liquid dispensing system can comprise a container configured to have a liquid disposed therein, and a penetrating tip configured to penetrate the container, wherein relative movement of the penetrating tip and the container toward one another is operable to create an opening in a portion of the container, and wherein the liquid dispenses from the container through the opening.

In one embodiment, the penetrating tip is disposed in the container.

In one embodiment, the liquid dispensing system can further comprise a plunger configured to be disposed within the container and form a seal about an inner surface of the container, wherein the plunger and the inner surface define a volume in the container that initially includes the liquid, and wherein the plunger is movable to cause the penetrating tip to create the opening and to cause the plunger to reduce the volume and dispense the liquid from the container through the opening.

In one embodiment, the plunger is associated with the penetrating tip.

In one embodiment, the penetrating tip is located outside the container.

In one embodiment, the penetrating tip comprises a plurality of penetrating tips, and wherein the plurality of penetrating tips are coupled to a common support member and spaced apart to correspond with a plurality of receptacles to facilitate dispensing liquid from a plurality of containers to the plurality of receptacles.

In one embodiment, the penetrating tip penetrates the container at least twice.

In one embodiment, the liquid dispensing system can further comprise a receptacle to receive the liquid.

In one embodiment, the receptacle comprises a well of an electrophoresis gel.

In one embodiment, the penetrating tip is coupled to a support member and extends through a bottom of the receptacle.

In one embodiment, the penetrating tip is disposed above the gel.

In one embodiment, the penetrating tip is supported by a housing for the receptacle.

In one embodiment, the liquid is dispensed from the container to the receptacle within a sealed space.

In one embodiment, the liquid dispenses from the container through the opening while the penetrating tip extends through the opening.

In one embodiment, the liquid dispenses from the container through the opening after the penetrating tip has been withdrawn from the opening.

In one embodiment, the liquid is dispensed from the container by positive pressure within the container.

In one embodiment, the positive pressure is generated by disposing a lid on the container, by compressing walls of the container, by heating the container, or combinations thereof.

In one embodiment, the positive pressure is generated by the penetrating tip creating a top opening in a top portion of the container, forming a seal in the top opening, and extending into the container thereby displacing air in the container.

In one embodiment, the liquid is dispensed from the container by centrifugal force or gravity.

In one embodiment, the penetrating tip comprises a recess configured to provide a fluid passageway to facilitate dispensing the liquid from the container with the penetrating tip disposed in the opening.

In one embodiment, a liquid dispensing container support apparatus can comprise a support structure, and an opening extending through the support structure and having a top portion and a bottom portion, wherein the top portion is configured to receive and support a container disposed therein and the bottom portion is configured to be disposed over a receptacle, such that liquid dispensed from the container passes into the receptacle.

In one embodiment, the opening comprises a plurality of openings, and wherein the plurality of openings are spaced apart to correspond with a plurality of receptacles to facilitate dispensing liquid from a plurality of containers to the plurality of receptacles.

In one embodiment, the top portion of e opening is configured to interface with the container.

In one embodiment, the top portion of the opening is configured to form a seal the container and define, at least in part, a sealed space for dispensing liquid from the container to the receptacle.

In one embodiment, a liquid dispensing container support apparatus can further comprise a sleeve configured to interface with the container and the top portion of the opening.

In one embodiment, a liquid dispensing container support apparatus can further comprise a second sleeve configured to interface with a second container and the top portion of the opening, wherein the second container has a different size than the first container, and the first sleeve and the second sleeve comprise adapters to facilitate use of different sized containers in the opening.

In one embodiment, the sleeve is configured to form a seal between the container and the top portion of the opening and define, at least in part, a sealed space for dispensing liquid from the container to the receptacle.

In one embodiment, a liquid dispensing container support apparatus can further comprise a vent channel to relieve gas pressure in the opening as the container is disposed in the opening.

In one embodiment, the support structure is configured to interface with a housing for the receptacle.

In one embodiment, the support structure is removably attachable with the housing.

In one embodiment, the support structure is integrally formed with a housing for the receptacle.

In one embodiment, a liquid dispensing container support apparatus can further comprise a seal disposed about the upper portion of the opening to retain the container, prevent contaminants from passing into or out of the receptacle, or combinations thereof.

In one embodiment, a liquid dispensing container support apparatus can further comprise a penetrating tip coupled to the support member and configured to be disposed over a bottom of the receptacle and to penetrate a bottom of the container, wherein relative movement of the penetrating tip and the container toward one another is operable to create a fluid opening in the bottom of the container, and wherein liquid dispenses from the container to the receptacle through the fluid opening.

In one embodiment, the liquid dispenses from the container to the receptacle through the fluid opening white the penetrating tip is engaged in the fluid opening In one embodiment, a liquid dispensing container support apparatus can further comprise a pressure generator within the container, selected from movement of a penetrating tip within the container, closing the cap of the container, compressing the walls of the container or heating the container.

In one embodiment, a method of dispensing a liquid from a container containing the liquid can comprise forming an opening in a portion of the container, and dispensing the liquid from the container through the opening.

In one embodiment, an opening is formed from inside the container.

In one embodiment, an opening is formed from outside the container.

In one embodiment, an opening is formed from both inside and outside the container.

In one embodiment, forming an opening comprises at least one of penetrating, piercing, puncturing, and rupturing a portion of the container.

Of course, it is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A liquid dispensing system, comprising:
   a support member;
   a plurality of penetrating tips fixedly coupled to the support member, each penetrating tip operable to penetrate a container having a liquid disposed therein and create an opening in a portion of the container to dispense the liquid; and
   a plurality of receptacles, each receptacle comprising a well of an electrophoresis gel configured to receive the liquid dispensed from the container.

2. The system of claim 1, wherein each of the plurality of penetrating tips is adapted to be disposed in the container.

3. The system of claim 2, further comprising a plurality of plungers, each plunger configured to be disposed within the container and form a seal about an inner surface of the container, wherein the plunger and the inner surface define a volume in the container that initially includes the liquid, and wherein the plunger is movable to cause one of the plurality of penetrating tips to create the opening and to cause the plunger to reduce the volume and dispense the liquid from the container through the opening.

4. The system of claim 3, wherein the plurality of plungers are associated with the plurality of penetrating tips.

5. The system of claim 1, wherein the plurality of penetrating tips are adapted to penetrate the container from a location outside the container.

6. The system of claim 5, wherein the plurality of penetrating tips are adapted to penetrate the container at least twice.

7. The system of claim 1, wherein the plurality of penetrating tips are spaced apart to correspond with a plurality of receptacles to facilitate dispensing liquid from a plurality of containers to the plurality of receptacles.

8. The system of claim 1, wherein the plurality of penetrating tips are configured to extend through a bottom of the receptacle.

9. The system of claim 1, wherein the plurality of penetrating tips are disposed above the gel.

10. The system of claim 1, wherein the plurality of penetrating tips are supported by a housing for the receptacle.

11. The system of claim 1, wherein the receptacle is adapted to form a sealed space with the container within which the liquid is dispensed.

12. The system of claim 1, wherein the liquid dispenses from the container through the opening while the penetrating tip extends through the opening.

13. The system of claim 1, wherein the liquid dispenses from the container through the opening after the penetrating tip has been withdrawn from the opening.

14. The system of claim 1, wherein each of the plurality of penetrating tips is operable to form the opening such that the liquid is dispensed from the container by positive pressure within the container.

15. The system of claim 14, wherein the positive pressure is generated by disposing a lid on the container, by compressing walls of the container, by heating the container, or combinations thereof.

16. The system of claim 14, wherein the positive pressure is generated by at least one of the plurality of penetrating tips creating a top opening in a top portion of the container, forming a seal in the top opening, and extending into the container thereby displacing air in the container.

17. The system of claim 1, wherein the liquid is dispensed from the container by centrifugal force or gravity.

18. The system of claim 1, wherein each penetrating tip comprises a recess configured to provide a fluid passageway to facilitate dispensing the liquid from the container with the penetrating tip disposed in the opening.

19. A liquid dispensing container support apparatus, comprising:
   a support structure;
   a plurality of penetrating tips fixedly coupled to the support structure, each penetrating tip operable to penetrate a container having a liquid disposed therein;
   a plurality of receptacles, each receptacle comprising a well of an electrophoresis gel configured to receive the liquid dispensed from the container; and
   an opening extending through the support structure and having a top portion and a bottom portion, wherein the top portion is configured to receive and support the container and the bottom portion is configured to be disposed over one of the plurality of receptacles to receive the liquid dispensed from the container.

20. The apparatus of claim 19, wherein the opening comprises a plurality of openings, and wherein the plurality of openings are spaced apart to correspond with the plurality of receptacles to facilitate dispensing liquid from a plurality of containers to the plurality of receptacles.

21. The apparatus of claim 19, wherein the top portion of the opening is configured to interface with the container.

22. The apparatus of claim 21, wherein the top portion of the opening is configured to form a seal with the container and define, at least in part, a sealed space for dispensing liquid from the container to one of the plurality of receptacles.

23. The apparatus of claim 21, further comprising a sleeve configured to interface with the container and the top portion of the opening.

24. The apparatus of claim 19, further comprising a vent channel to relieve gas pressure in the opening as the container is disposed in the opening.

25. A method of loading a sample into an electrophoresis gel, comprising:
   forming an opening in a portion of a container using at least one of a plurality of penetrating tips that are fixedly coupled to a support member; and
   dispensing the liquid from the container through the opening into a well of an electrophoresis gel.

26. The method of claim 25, wherein an opening is formed from inside the container.

27. The method of claim 25, wherein an opening is formed from outside the container.

28. The method of claim 25, wherein an opening is formed from both inside and outside the container.

29. The method of claim 25, wherein forming an opening comprises at least one of penetrating, piercing, puncturing, and rupturing a portion of the container.

\* \* \* \* \*